United States Patent [19]

Fischer et al.

[11] 3,957,730
[45] May 18, 1976

[54] RECOVERY OF PURE 2-METHYL-2-HYDROXY-HEPTANONE-6

[75] Inventors: Roman Fischer, Mutterstadt; Hermann Overwien, Ludwigshafen; Axel Nissen, Heidelberg, all of Germany

[73] Assignee: BASF Aktiengesellschaft, Ludwigshafen, (Rhine), Germany

[22] Filed: Sept. 16, 1974

[21] Appl. No.: 506,290

[30] Foreign Application Priority Data
Oct. 17, 1973  Germany............................ 2352054

[52] U.S. Cl............................. 260/594; 260/345.1
[51] Int. Cl.$^2$........................................ C07C 45/24
[58] Field of Search................. 260/593, 594, 345.1
[56] References Cited
UNITED STATES PATENTS
3,686,321   8/1972   Mueller et al. ..................... 260/593

FOREIGN PATENTS OR APPLICATIONS
2,113,056   10/1971   France

OTHER PUBLICATIONS
Hickenbottom, "Reactions of Organic Compounds," pp. 136–143 (1957).

*Primary Examiner*—James O. Thomas, Jr.
*Assistant Examiner*—James H. Reamer
*Attorney, Agent, or Firm*—Johnston, Keil, Thompson & Shurtleff

[57] ABSTRACT

A process for the recovery of pure 2-methyl-2-hydroxyheptanone-6 by conversion of impure 2-methyl-2-hydroxyheptanone-6 into 2,2,6-trimethyl 2,3-hydro-4-H-pyran by treatment with an acid which is not volatile under the reaction conditions at a temperature of from 30° to 150°C, purification of the 2,2,-6-trimethyl-2,3-hydro-4-H-pyran thus obtained by distillation, reaction of the purified 2,2,6-trimethyl-2,3-hydro-4-H-pyran with water in the presence of an acid ion exchanger and removal of the excess water from the aqueous solution of 2-methyl-2-hydroxyheptanone-6 thus obtained by distillation. 2-methyl-2-hydroxyheptanone-6 is suitable for the production of 2-methyl-2-hydroxy-6-aminoheptane which is effective as a pharmaceutical for conditions of the heart and circulation.

7 Claims, No Drawings

RECOVERY OF PURE 2-METHYL-2-HYDROXY-HEPTANONE-6

The invention relates to a process for the recovery of pure 2-methyl-2-hydroxyheptanone-6 from impure 2-methyl-2-hydroxyheptanone-6.

A number of methods are known for the production of 2-methyl-2-hydroxyheptanone-6, for example the acid-catalyzed addition of water to 2-methylhepten-2-one-6 (cf. J. Amer. Chem. Soc., 77, (1955), page 1617 and French Patent 1,511,021), reaction of δ-caprolactam with methyl magnesium bromide (cf. Chemical Abstracts, volume 53, paragraph 9280c), reaction of the monooxime of heptanedione-2,6 with methyl magnesium bromide followed by hydrolysis (cf. Japanese Patent Publication 24067/61), reaction of 2-methylpenten-4-ol-3 acetate with ethyl acetate and benzyl peroxide (cf. Chemical Abstracts, volume 57, column 5791c) or reaction of 2-methyl-2-hydroxybutene-3 with acetone and water in the presence of ditertiarybutyl peroxide (cf. Japanese Patent Publication 18,724/65). 2-Methyl-2-hydroxyheptanone-6 which is devoid of other organic substances or salts is not obtained by any of the said syntheses. Purification purely by distillation is inadequate because it can only be carried out with considerable loss of yield, 2-methyl-2-hydroxyheptanone-6 having a marked tendency to decompose. In many cases, for example when using 2-methyl-2-hydroxyheptanone-6 for the production of pharmaceuticals, it is necessary to start from pure 2-methyl-2-hydroxyheptanone-6.

It is an object of the invention to provide a process by which pure 2-methyl-2-hydroxyheptanone-6 is obtained in a simple manner from mixtures containing the same. Another object of the invention is to provide a process in which there is practically no loss of yield in the purification of 2-methyl-2-hydroxyheptanone-6.

In accordance with this invention these and other objects and advantages are achieved in a process for the recovery of pure 2-methyl-2-hydroxyheptanone-6 which comprises converting impure 2-methyl-2-hydroxyheptanone-6 into 2,2,6-trimethyl-2,3-hydroxy-4-H-pyran by treatment with an acid which is not volatile under the reaction conditions at a temperature of from 30° to 150°C, purifying the 2,2,6-trimethyl-2,3-hydro-4-H-pyran thus obtained by distillation, reacting the purified 2,2,6-trimethyl-2,3-hydro-4-H-pyran with water in the presence of an acid ion exchanger and removing the excess of water from the aqueous solution of 2-methyl-2-hydroxyheptanone-6 thus obtained by distillation.

The starting material in the process according to the invention is contaminated 2-methyl-2-hydroxyheptanone-6 such as is obtained by the said prior art methods, for example a reaction product from the addition of water to 2-methylhepten-2-one-6 which has been neutralized to pH 8; another suitable starting material is the residue which is obtained in the reaction of acetone, isobutylene and aqueous formaldehyde after distilling off the 2-methylhepten-1-one-6 by the method described in German Patent 1,259,876. Such a residue as a rule contains from 20 to 60% by weight of 2-methyl-2-hydroxyheptanone-6 and unidentified impurities. Residues containing 2-methyl-2-hydroxyheptanone-6 are also suitable which have been obtained in the reaction of isobutylene with aqueous methyl vinyl ketone (cf. German Patent 973,089) or by reaction of isobutylene with 1-hydroxybutanone-3 (cf. German Patent 1,277,848) or by reaction of 2-methylketone-1-ol-4 with acetone after the 2-methylhepten-1-one-6 has been distilled off (cf. German Patent 1,286,020). The impurities contained in 2-methyl-2-hydroxyheptanone-6 used as starting material have not been identified.

Contaminated 2-methyl-2-hydroxyheptanone-6 is converted by treatment with an acid which is not volatile under the reaction conditions into 2,2,6-trimethyl-2,3-hydro-4-H-pyran. It is preferred to use mineral acids which have little or no volatility such as phosphoric acid or sulfuric acid or carboxylic acids having little or no volatility. Examples of suitable carboxylic acids are $C_5$ to $C_{20}$ alkanoic acids, alkane dicarboxylic acids of up to 24 carbon atoms, mono or dibasic cyclohexanoic acids, benzene carboxylic acids and naphthalene carboxylic acids. Non-volatile mineral acids such as phosphoric acid or alkane dicarboxylic acids of up to six carbon atoms are particularly suitable. It has proved to be advantageous to use the said acids in an amount of from 0.001 to 5% particularly from 0.03 to 0.5% by weight based on the starting mixture used. It is also possible to use acid ion exchangers, for example crosslinked polystyrene which contains carboxylic acid groups or particularly sulfo groups, instead of the said mineral acids.

The reaction is advantageously carried out at a temperature of from 30° to 150°C and particularly from 95° to 115°C. It has proved to be advantageous to remove 2,2,6-trimethyl-2,3-hydro-4-H-pyran formed from the reaction mixture at the rate at which it is formed. The said product is conveniently distilled off continuously from the reaction mixture and the distillation is generally promoted by introducing steam.

The 2,3,6-trimethyl-2,3-hydro-4-H-pyran thus obtained is purified. Purification is conveniently carried out by distillation and as a rule use is made of columns having ten to thirty theoretical trays with a pressure of from 20 to 200 mm Hg, bottoms temperatures of from 60° to 130°C and top temperatures of from 40° to 110°C.

The pure 2,2,6-trimethyl-2,3-hydro-4-H-pyran thus obtained is then treated with water in the presence of an acid ion exchanger. It is preferable to use from one mole to three moles of water for each mole of pyran. The treatment is carried out as a rule at a temperature of from 0° to 100°C and a temperature of from 20° to 70°C is particularly suitable. Examples of suitable ion exchangers are crosslinked polystyrene containing carboxylic acid groups or sulfo groups or for example an ion exchanger prepared on the basis of acrylic acid. It is particularly preferred to use an ion exchanger which contains carboxylic acid groups as the active groups.

The aqueous solution of 2-methyl-2-hydroxyheptanone-6 thus obtained, which as a rule contains from 80 to 95% by weight of the said compound, is freed from water by distillation. Columns having from 1 to 3 theoretical trays are generally used. A falling film evaporator has proved to be especially convenient. It is preferred to use temperatures of from 60° to 100°C and pressures of from 50 to 200 mm for the purpose.

The pure 2-methyl-2-hydroxyheptanone-6 prepared according to the process of the invention is suitable for the production of 2-methyl-2-hydroxy-6-aminoheptane which is effective as a pharmaceutical for heart and circulatory affections (cf. German Laid-Open Specification (DOS) No. 2,055,813, U.S. Pat. No. 2,457,656, French Patent 1,511,021 and Japanese Patent Publication 21308/1961).

The process according to the invention is illustrated in the following Examples.

EXAMPLE 1

100 kg of a residue which has been obtained in the synthesis of methylheptanone according to German Patent No. 1,259,876 and which contains 29% by weight of 2-methyl-2-hydroxyheptanone-6 is distilled with an addition of 3.33 kg of water and 0.034 kg of 98% by weight phosphoric acid in a column having twenty theoretical trays at a pressure of 760 mm. A temperature of 120°C is maintained in the bottoms and of 105°C at the top. The aqueous phase which separates in the receiver is continually returned to the distillation. Distillation is carried on until 2,2,6-trimethyl-2,3-dihydro-4-H-pyran no longer separates in the receiver. 28 kg of 2,2,6-trimethyl-2,3-dihydro-4-H-pyran is obtained with a purity of 90%

EXAMPLE 2

100 kg of 2-methylhepten-2-one-6 is hydrated with sulfuric acid as catalyst as described in J. Amer. Chem. Soc., 6, 1955, page 1617. The reaction mixture is then neutralized to pH 8, the aqueous phase is separated and the upper organic phase is acidified to pH 6 with 20% by weight aqueous adipic acid solution. Distillation of the solution obtained is carried out as described in Example 1. 96 kg of 2,2,6-trimethyl-2,3-dihydro-4-H-pyran of a purity of 91% by weight is obtained as distillate.

EXAMPLE 3

Crude 2,2,6-trimethyl-2,3-hydro-4-H-pyran obtained according to Example 1 or 2 is fractionally distilled in a column having 20 theoretical trays at 100 mm. A temperature of 72°C and a reflux ratio of 1:5 are maintained at the top. 88 kg of 2,2,6-trimethyl-2,3-dihydro-4-H-pyran having a purity of more than 99% is obtained from 100 kg of starting material.

EXAMPLE 4

100 kg of pure 2,2,6-trimethyl-2,3-hydro-4-H-pyran as obtained according to Example 3 is stirred for two hours at 70°C with 28.6 kg of distilled water and 1 kg of an ion exchanger having carboxylic acid groups as active centers in acid form. The ion exchanger is then separated. An 89 to 90% by weight mixture of 2-methyl-2-hydroxyheptanone-6 with water is obtained which is devoid of other compounds. The water is removed from the solution thus obtained in a falling film evaporator at 80° and at a pressure of 100 mm. 114 kg of pure 2-methyl-2-hydroxyheptanone-6 is obtained.

We claim:

1. A process for the recovery of pure 2-methyl-2-hydroxyheptanone-6 which comprises converting contaminated 2-methyl-2-hydroxyheptanone-6 into 2,2,6-trimethyl-2,3-hydroxy-4-H-pyran by treatment with 0.001 to 5% by weight, based on the starting mixture used, of an acid which is not volatile under the reaction conditions and is selected from the group consisting of sulfuric acid, phosphoric acid and an alkane dicarboxylic acid of up to six carbon atoms at a temperature of from 30° to 150°C, purifying the 2,2,6-trimethyl-2,3-hydro-4-H-pyran thus obtained by distillation, reacting the purified 2,2,6-trimethyl-2,3-hydro-4-H-pyran with water in the presence of an acid ion exchanger having sulfo or carboxylic acid ion exchange groups to convert said pyran into 2-methyl-2-hydroxyheptanone-6 and removing excess water by distillation from the aqueous solution of 2-methyl-2-hydroxyheptanone-6 thus obtained.

2. A process as claimed in claim 1 wherein phosphoric acid or an alkane dicarboxylic acid of up to six carbon atoms is used as the non-volatile acid in the conversion of 2-methyl-2-hydroxyheptanone-6 into 2,2,6-trimethyl-2,3-hydro-4-H-pyran.

3. A process as claimed in claim 1 wherein a temperature of from 95° to 115°C is used for the conversion of 2-methyl-2-hydroxyheptanone-6 to 2,2,6-trimethyl-2,3-hydro-4-H-pyran.

4. A process as claimed in claim 1 wherein 2,2,6-trimethyl-2,3-hydro-4-H-pyran is removed from the reaction mixture at the rate at which it is formed.

5. A process as claimed in claim 1 wherein said acid ion exchanger has carboxylic acid ion exchange groups.

6. A process as claimed in claim 1 wherein the reaction of water and said pyran is conducted by using 1 to 3 mols of water per mol of said pyran.

7. A process as claimed in claim 1 wherein the 2,2,6-trimethyl-2,3-hydro-4-H-pyran is reacted with water in the presence of said acid ion exchanger at a temperature of from 0° to 100°C.

* * * * *